United States Patent [19]

Giorgio et al.

[11] Patent Number: 4,631,254

[45] Date of Patent: Dec. 23, 1986

[54] CARCINOEMBRYONIC ANTIGEN DETERMINATION

[75] Inventors: Nicholas A. Giorgio, Avenel; John Krupey, Glen Rock; Leonard T. Wilson, Verona, all of N.J.

[73] Assignee: Hoffmann-La Roche Inc., Nutley, N.J.

[21] Appl. No.: 773,263

[22] Filed: Sep. 6, 1985

Related U.S. Application Data

[63] Continuation of Ser. No. 446,925, Dec. 6, 1982, abandoned.

[51] Int. Cl.$^4$ ............... G01N 33/53; G01N 33/539; G01N 33/541; G01N 33/574

[52] U.S. Cl. ..................... 435/7; 436/175; 436/177; 436/534; 436/540; 436/804; 436/813; 436/825; 436/826

[58] Field of Search ............ 435/7; 436/175, 177, 436/534, 540, 804, 813, 825, 826

[56] References Cited

U.S. PATENT DOCUMENTS

| | | |
|---|---|---|
| 3,776,698 | 12/1973 | Eisentraut ............... 424/111 X |
| 3,852,415 | 12/1974 | Vandervoorde ............... 436/813 X |
| 4,056,468 | 11/1977 | Breiter ............... 436/178 X |
| 4,140,753 | 2/1979 | Edgington ............... 436/813 X |
| 4,180,556 | 12/1979 | Kim ............... 436/531 X |
| 4,246,351 | 1/1981 | Miyake ............... 435/180 X |
| 4,272,504 | 6/1981 | Kim ............... 436/531 |
| 4,298,472 | 11/1981 | Durand ............... 436/178 X |
| 4,299,815 | 11/1981 | Hansen ............... 436/540 |
| 4,467,031 | 8/1984 | Gallati ............... 436/813 X |
| 4,578,349 | 3/1986 | Schaffel ............... 436/177 X |

FOREIGN PATENT DOCUMENTS 0440558 12/1935 United Kingdom .

Primary Examiner—Sidney Marantz
Attorney, Agent, or Firm—Jon S. Saxe; George M. Gould; Dennis P. Tramaloni

[57] ABSTRACT

Process for the determination of carcinoembryonic antigen (CEA) in a sample of serum or plasma. The process comprises contacting a slightly acidic buffered sample of the serum or plasma with hydrophilic silica at room temperature, separating the silica from the sample and carrying out a radioimmunoassay for carcinoembryonic antigen on said sample.

12 Claims, No Drawings

CARCINOEMBRYONIC ANTIGEN DETERMINATION

This is a continuation of application Ser. No. 446,925 filed Dec. 6, 1982, abandoned.

BACKGROUND OF THE INVENTION AND STATEMENT OF PRIOR ART

The determination of carcinoembryonic antigen (hereinafter CEA) is well documented in the art. It is likewise well established that certain non-specific interfering substances present in the sample to be tested must be substantially removed or neutralized in some manner in order for the determination to be accurate and sensitive.

There are a number of procedures known in the art by which potentially interfering substances present in a sample of biological fluid, e.g., serum or plasma, can be removed or neutralized before testing for CEA. It is clearly an advantage to simplify the manipulations required to remove such interfering substances in a given assay in terms of time, cost, and relative ease in conducting the test.

More particularly, in the determination of CEA as taught in Freedman, et al., U.S. Pat. No. 3,663,684, a blood sample is initially treated with a glycoprotein solvent in which CEA is soluble, and the resulting solution is clarified. Examples of such solvents include perchloric acid, trichloroacetic acid, phosphotungstic acid, and the like. The purpose of treating the blood sample with the glycoprotein solvent is to remove precipitable normal proteins and interfering antigenic materials. The precipitated interfering protein material is thereafter removed from the sample by centrifugation and removal of the acid is accomplished by either dialysis or gel filtration. Both of these methods are time-consuming, expensive, and technically tedious. The number of manipulative steps also adds to the imprecision of the assay.

In accordance with the present invention, a method is disclosed for the pretreatment of a sample of human serum or plasma for assay for determination of CEA which is more rapid, easier, and less expensive than the preparative methods known in the art.

DETAILED DESCRIPTION OF THE INVENTION

In accordance with the present invention, a method of preparing samples of human serum or plasma for assay for carcinoembryonic antigen (CEA), is described which is rapid, convenient, and less expensive than methods used heretofore. The method of the present invention comprises diluting the sample with a buffer solution to a slightly acid pH, mixing the sample with hydrophilic silica at room temperature, allowing the mixture to stand for a short period of time, and separating the silica from the sample. Within the scope of the present invention is an improved assay for CEA incorporating the herein disclosed preparative methodology.

The hydrophilic silica employed in the methodology of the present invention is characterized by having a large specific surface area and a relatively small average primary particle size. The specific surface area of the silica useful in the methodology of the present invention is from about 100 to about 400 m$^2$/g, and preferably from about 130 to about 380 m$^2$/g. The surface area of the silica is determined according to the method of Brunauer, et al., J.A.C.S. 60, 309 (1958). The average primary particle size of the silica used in the practice of this invention is from about 7-16 nanometer (millimicron).

The amount of silica employed in the practice of the invention varies from 10 mg to 100 mg and preferably 35 mg to 80 mg.

The preparatory method of the present invention comprises diluting a sample of from about 0.2 to about 0.5 ml of plasma or serum.

The dilution of the test sample with an acidic buffer is necessary to maximize the sensitivity of the assay. The sample, thus diluted, will have a slightly acidic pH, i.e., a pH from about 6.0 to about 6.5 and preferably 6.3. Examples of buffers which can be used in the present invention include conventional acidic buffers, such as, for example, an ammonium acetate buffer, sodium acetate, sodium citrate, and the like, would be suitable. A sufficient amount of the buffer is utilized to assure that the pH of the sample is slightly acidic, i.e., a pH of from about 6.0 to about 6.5.

The method of the present invention eliminates the perchloric acid extraction step and the necessity of dialysis to purify the perchloric acid treated specimen. The significant savings in time and cost resulting from the use of the preparatory method of the present invention make possible assays for CEA on a relatively large scale, e.g., for mass screening. A complete assay for CEA incorporating the preparatory method of the present invention can be conducted in about four hours. This represents a significant improvement over the commercial CEA assay utilizing dialysis which must be run overnight.

The sample preparatorily treated in accordance with the present invention is thereafter subject to the appropriate assay for CEA. The choice of a particular type of immunoassay for CEA to be utilized is not critical to the preparatory method of the invention. Generally, a radioimmunoassay or enzyme immunoassay is preferred with a radioimmunoassay being particularly preferred.

In general, a determination of CEA in accordance with the present invention comprises:

(a) preparing a sample of serum or plasma from a patient as disclosed herein to neutralize potentially interfering materials;

(b) adding an excess of an antibody to CEA to the samples to be tested and incubating for a predetermined time;

(c) adding labeled CEA to the samples and incubating for a predetermined time;

(d) adding to the mixture of (b) and (c) an insolubilizing agent thereby forming a solid phase containing antibody-bound CEA and a liquid phase containing unbound CEA;

(e) separating said solid and liquid phases;

(f) determining the amount of said label in either said solid or said liquid phase; and (g) determining the amount of CEA present in the sample by comparison to a standard.

In the above determination the term "neutralize" interfering materials is utilized. It will, of course, be appreciated that such term is intended to mean treatment in accordance with the present invention, as well as the various prior art procedures whereby such materials are physically removed from the sample, since the effect in each instance is the same. Therefore, the term, in essence, means that the immunological effect of such interfering materials is negated.

As previously stated, the label utilized to label the CEA in the aforementioned determination may be any immunologically compatible labeling substance amenable to quantitative determination, such as, for example, a radioisotope, an enzyme, a fluoroescent or chemiluminescent substance and the like. Enzyme and radioisotope labels are preferred with the latter being particularly preferred. Among the radioisotopes conventionally utilized for radioimmunoassays, the isotopes of iodine are preferred with iodine-125 being particularly preferred.

The insolubilizing agent utilized to form a solid phase containing antibody-bound CEA and a liquid phase containing unbound CEA can be any material conventionally recognized in the art for such purpose. For example, certain aliphatic alcohols, ion exchange resins and inorganic salts, as well as antibodies to the CEA antibody, will cause the formation of a protein precipitate which contains antibody-bound CEA. A preferred insolubilizing agent is second antibody, i.e., antibody to the CEA antibody, in immobilized, i.e., insolubilized, form.

With regard to the immobilization of second antibody discussed above, any of the numerous techniques recognized in the art for insolubilization of an immunological component, such as particles of various sizes, beads, sticks, or a strip of support medium, may be utilized. It will be appreciated that, wherein a particular insolubilization material is polymeric in nature, e.g., a styrene polymer or copolymer, it may be utilized in more than one of the above-given forms, depending on its properties. A particularly preferred material for immobilization of the second antibody is unsintered poly(vinylidene fluoride) which may be utilized, for example, in finely particulate form or as a film. The antibody may be physically adsorbed onto the immobilizing material or chemically bound thereto by methods conventional in the art.

The particular proportions, incubation times and temperatures utilized for a given determination of CEA are considered to be within the skill of the art given the large body of knowledge published with regard to CEA. Preferred incubations for reaction of the antiserum and the subsequent reaction with labeled CEA are from about 1 hour to about 2.5 hours with 2 hours being particularly preferred. These incubations are carried out at a temperature of about 45° C. Wherein an enzyme label is utilized, adjustment in the incubation time and particularly the temperature may be required to prevent inactivation of the enzyme, if it is labile at the temperatures suggested herein. Wherein immobilized second antibody is utilized as the insolubilizing agent, the samples are preferably incubated at ambient temperature for from about 10 to 30 minutes preferably about 15 minutes. The determination of CEA in the sample is made by comparison to a standard curve as is conventional in the art. Reading of the label concentration is likewise carried out by conventional means depending on the type of label, e.g., by use of a gamma scintillation spectrometer where a radionuclide label is utilized.

The following Examples further illustrate the invention. Unless otherwise indicated, all temperatures are in degrees Centigrade.

EXAMPLE 1

The commercial determination for CEA was carried out as follows:

Samples (0.5 ml.) of plasma (in duplicate) from suspected colon cancer patients were extracted with 2.5 ml. of cold 1.2 molar perchloric acid by mixing in a vortex-type mixer for 30 seconds and then centrifuging at 1,000×gravity for 20 minutes. The supernatants were collected and transferred to dialysis bags and dialyzed against deionized water changing the water three times with a minimum of three hours between changes. A final dialysis was carried out utilizing an ammonium acetate buffer, pH about 6.5. After dialysis, the contents of the dialysis bags were transferred to test tubes and 25 $\mu$l. of commercial CEA antiserum added to each with mixing in a vortex mixer. The tubes were incubated at 45° for 30 minutes. To each tube was added 25 $\mu$l. $^{125}$I-CEA with mixing and the tubes again incubated at 45° for 30 minutes. A total of 2.5 ml. of zirconyl phosphate gel, pH 6.25, was added to each tube, and the contents centrifuged at 1,000×gravity for 5 minutes. The supernatants were removed and 5 ml. of ammonium acetate buffer, pH 6.25, were added with mixing. The contents of the tubes were again centrifuged as before and the supernatants removed. The amount of bound $^{125}$I-CEA in the remaining gel was determined by counting with a gamma scintillation spectrometer for one minute.

A standard inhibition curve was prepared as follows:

To pairs of test tubes was added 5.0 ml. of a 1 to 10 dilution of EDTA buffer (pH 6.5) with deionized water. To each pair of tubes was added CEA standard dose, i.e., 0, 10, 25, 50, and 100 $\mu$l. equivalent to 0, 2.5, 6.25, 12.5, and 25 ng/ml. of CEA activity and the contents mixed with a vortex-type mixer. The tubes were then treated with antisera to CEA and $^{125}$I-CEA as above. The readings were taken and a curve established for comparison of the readings obtained with the samples of patient plasma.

EXAMPLE 2

A determination of CEA in accordance with the present invention was carried out as follows:

Samples (0.5 ml.) of plasma were diluted with 2.9 ml. of 5.2 mM ammonium acetate buffer (pH 4) and mixed on a vortex mixer. Add 1.7 ml. of a 5% aqueous suspension of silica (having a BET surface area of about 380 m$^2$/g and an average primary particle size of about 7 nm) and vortex thoroughly until the sample is homogeneous. Incubate the sample at ambient temperature for about 10 minutes. The sample is centrifuged at 1,000×g for about 10 minutes, and the supernate is decanted into another tube. To each tube was added 25 $\mu$l. of commercial CEA antiserum with mixing in a vortex mixer. The tubes were incubated at 45° C. for about 1 hour. To each tube was added 25 $\mu$l. of $^{125}$I-CEA with mixing and the tubes again incubated for about 1.5 hours at 45° C. To each tube is added 1 ml. of an aqueous suspension of antibody against the CEA antiserum insolubilized by adsorption on particles of poly(vinylidene fluoride). The tubes are again vortexed and incubated for about 15 minutes at room temperature. The samples were again centrifuged at 1000×g for 10 minutes. The supernatants were decanted, and the pellet counted in a gamma scintillation spectrometer.

A standard inhibition curve was prepared as follows:

To pairs of test tubes was added 0.5 ml. of human plasma containing <1 ng/ml. CEA. To each pair of tubes was added CEA standard dose, i.e., 0, 10, 25, 50, and 100 $\mu$l. equivalent to 0, 2.5, 6.25, 12.5, and 25 ng/ml. of CEA activity, and the contents mixed on a vortex-type mixer. These tubes were treated with ammonium acetate buffer, silica, antisera to CEA $^{125}$I-CEA and insobilized second antibody as above. The readings were taken and a curve established for comparison of the readings obtained with the samples of patient plasma.

In Table I, the results for the samples prepared in accordance with the commercial dialysis method of Example I and the method of the subject invention, Example 2, were compared.

TABLE I

Comparison of Standard CEA Assay (Example 1) and CEA determination with the present invention (Example 2)

| Tubes | Example 1 Standard CEA Assay (CPM)* | % Bo* | Example 2 New CEA Assay (CPM)* | % Bo** |
|---|---|---|---|---|
| Total $^{125}$I-CEA | 123,000 | | 123,000 | |
| Non-Specific Binding | 3,600 | | 3,600 | |
| Binding 0 CEA (Bo) | 87,800 | | 64,800 | |
| Binding 2.5 ng/ml. CEA | 78,600 | 89% | 60,000 | 93% |
| Binding 6.25 ng/ml. CEA | 60,000 | 68% | 45,800 | 70% |
| Binding 12.5 ng/ml. CEA | 42,200 | 48% | 31,900 | 49% |
| Binding 25 ng/ml. CEA | 26,700 | 50% | 24,600 | 38% |
| CEA Medium Control 7.0 ng/ml. | — | | 7.8 ng/ml. | |
| CEA High Control 14.6 ng/ml. | — | | 15.4 ng/ml. | |

*(CPM) = Counts Per Minute
**% Bo = Percentage of binding of CEA to antibody at zero antigen concentration

EXAMPLE 3

A determination of CEA in accordance with the present invention was carried out as follows:

A sample (0.2 ml) of plasma is added to a 13×100 mm glass tube. To this sample is added 2.3 ml. of a 1.85% w/v suspension of silica (having a BET surface area of about 380 m$^2$/g and an average primary particle size of about 7 nm) in 3.3 mM ammonium acetate buffer, pH 4. The sample is vortexed thoroughly until the sample is homogeneous. The sample is incubated at ambient temperature for about 15 minutes. The sample is centrifuged at 1,000×g for about 5 minutes, and the supernate is decanted into another tube. To each tube was added 25 µl. of goat anti-CEA antiserum with mixing in a vortex mixer. The tubes are incubated at 45° C. for about 1 hour. To each tube was added 25 µl. of $^{125}$I-CEA with mixing, and the tubes again incubated for about 1.5 hours at 45° C. To each tube is added 0.6 ml. of an aqueous suspension of antibody against the CEA antiserum insolubilized by adsorption on particles of poly(vinylidene fluoride). The tubes are again vortexed and incubated for about 15 minutes at room temperature. The samples were again centrifuged at 1,000×g for 10 minutes. The supernatants were decanted, and the pellet counted in a gamma scintillation spectrometer.

A standard inhibition curve was prepared as follows:

To pairs of test tubes were added 0.2 ml. of human plasma containing less than 1 ng/ml. CEA. To each pair of tubes was added CEA standard dose, i.e., 0, 10, 25, 50, and 100 µl. equivalent to 0, 2.5, 6.25, 12.5, and 25 ng/ml. of CEA activity, and the contents mixed on a vortex-type mixer. The tubes were treated with antisera to CEA, $^{125}$I-CEA and insolubilized second antibody as above. The readings were taken and a curve established for comparison of the readings obtained with the samples of patient plasma.

In Table II, the results for the samples prepared in accordance with the commercial dialysis method of Example 1 and the method of the subject invention, Example 3, were compared.

TABLE II

Comparison of Standard CEA Assay (Example 1) and CEA determination with the present invention (Example 3).

| Tubes | Example 1 Standard CEA Assay (CPM)* | % Bo** | Example 3 New CEA Assay (CPM)* | % Bo** |
|---|---|---|---|---|
| Total $^{125}$I-CEA | 123,100 | | 135,800 | |
| Non-Specific Binding | 3,600 | | 3,800 | |
| Binding 0 CEA (Bo) | 87,800 | 100% | 86,000 | 100% |
| Binding 2.5 ng/ml. CEA | 78,600 | 89% | 80,000 | 93% |
| Binding 6.25 ng/ml. CEA | 60,000 | 68% | 65,900 | 77% |
| Binding 12.5 ng/ml. CEA | 42,200 | 48% | 52,500 | 61% |
| Binding 25 ng/ml. CEA | 26,700 | 30% | 37,000 | 43% |
| CEA Medium Control 7.0 ng/ml. | — | | 6.3 ng/ml. | |
| CEA High Control 14.6 ng/ml. | — | | 14.8 ng/ml. | |

*(CPM) = Counts Per Minute
**% Bo = Percentage of binding of CEA to antibody at zero antigen concentration

We claim:

1. A method of determining the concentration of carcinoembryonic antigen in a sample of serum or plasma from a human which comprises:
   (a) adding sufficient buffer to a sample of serum or plasma to produce a pH of from about 6.0 to about 6.5;
   (b) adding hydrophilic silica having a BET surface area of from 100 to 400 m$^2$/g and an average primary particle size of from 7–16 nanometer to said sample and incubating said sample to neutralize materials in said sample which would interfere with determination of CEA;
   (c) separating the silica from the sample;
   (d) adding an excess of an antibody to CEA to said sample and incubating for a predetermined time;
   (e) adding to said sample an amount of carcinoembryonic antigen labeled with a labeling substance capable of being quantitatively determined at least sufficient to react with the amount of antibody added in step (d) and incubating for a predetermined time;
   (f) adding to said sample an insolubilizing agent thus forming a solid phase containing antibody-bound CEA and a liquid phase containing unbound CEA;
   (g) separating said solid and liquid phases;
   (h) determining the amount of said labeling substance present in either said solid or said liquid phase; and
   (i) determining the amount of carcinoembryonic antigen present in said sample by comparison against a standard.

2. The method in accordance with claim 1 wherein the hydrophilic silica has a BET surface area of from about 130 to 380 m$^2$/g and an average primary particle size of from about 7–16 nanometer.

3. The method in accordance with claim 2 wherein the hydrophilic silica has a BET surface area of about 380 m$^2$/g and an average primary particle size of about 7 nm.

4. The method in accordance with claim 1 wherein the acidic buffer is ammonium acetate.

5. The method in accordance with claim 1 wherein the pH of the buffered sample is about 6.3.

6. The method in accordance with claim 1 wherein said insolubilizing agent is an antibody against the antibody in step (d), said antibody being in insolubilized form.

7. The method in accordance with claim 1 wherein said labeling substance is a radioisotope.

8. The method in accordance with claim 7 wherein said radioisotope is a radioisotope of iodine.

9. The method in accordance with claim 8 wherein said radioisotope of iodine is iodine-125.

10. The method in accordance with claim 1 wherein said labeling substance is an enzyme.

11. The method in accordance with claim 1 wherein said labeling substance is a fluorescent substance.

12. The method in accordance with claim 1 wherein said labeling substance is a chemiluminescent substance.

* * * * *